United States Patent
Pudota et al.

(10) Patent No.: US 11,237,100 B2
(45) Date of Patent: Feb. 1, 2022

(54) METHODS USING FTIR FOR PLANT TRAIT DETECTION AND TRAIT INTROGRESSION

(71) Applicant: Dow AgroSciences LLC, Indianapolis, IN (US)

(72) Inventors: Bala Bhaskar Pudota, Whitestown, IN (US); Daniel Gachotte, Indianapolis, IN (US); Virginia Stoltz, Indianapolis, IN (US); Terence A. Walsh, Carmel, IN (US)

(73) Assignee: Corteva Agriscience LLC, Indianapolis, IN (US)

( * ) Notice: Subject to any disclaimer, the term of this patent is extended or adjusted under 35 U.S.C. 154(b) by 549 days.

(21) Appl. No.: 15/601,157

(22) Filed: May 22, 2017

(65) Prior Publication Data

US 2017/0356019 A1 Dec. 14, 2017

Related U.S. Application Data

(60) Provisional application No. 62/347,728, filed on Jun. 9, 2016.

(51) Int. Cl.
  *G01N 21/35* (2014.01)
  *G01N 21/84* (2006.01)

(52) U.S. Cl.
  CPC ..... *G01N 21/35* (2013.01); *G01N 2021/3595* (2013.01); *G01N 2021/8466* (2013.01)

(58) Field of Classification Search
  CPC ............... G01N 2021/3595; G01N 2021/8466
  See application file for complete search history.

(56) References Cited

U.S. PATENT DOCUMENTS

| | | | |
|---|---|---|---|
| 6,646,264 B1* | 11/2003 | Modiano | G01N 21/359 250/339.07 |
| 8,063,269 B2* | 11/2011 | Shah | C12N 15/8247 435/320.1 |
| 2005/0250212 A1* | 11/2005 | Azizian | G01N 21/274 436/71 |

(Continued)

OTHER PUBLICATIONS

Xin, H. et al. "Mid-Infrared Spectral Characteristics of Lipid Molecular Structures in Brassica carinata Seeds: Relationship to Oil Content, Fatty Acid and Glucosinolate Profiles, Polyphenols, and Condensed Tannins," J. Agric. Food Chern. 2014, 62, 32, 7977-7988 (Year: 2014).*

(Continued)

*Primary Examiner* — Lyle Alexander
*Assistant Examiner* — Michelle Adams

(57) ABSTRACT

Provided are methods and/or systems having advantages of cost effective, time saving, and informative user-friendly characteristics to accomplish trait introgression. The methods provided comprise determining presence of omega-3 fatty acids (for example docosahexaenoic acid or DHA; docosapentaenoic acid or DPA; Alpha linolenic acid or ALA; and eicosapentaenoic acid or EPA) using Fourier Transformed infra Red (FTIR) spectrum. The use of FTIR enables analysis of the oil contained in the seeds using a multivariate-based Mid-FTIR model. The methods and/or systems provided advantages of non-destructive analysis to provide information to facilitate trait introgression and other breeding applications.

5 Claims, 3 Drawing Sheets

(56) References Cited

U.S. PATENT DOCUMENTS

2010/0143570 A1* 6/2010 Ripley ............... A01H 1/04
426/629

OTHER PUBLICATIONS

Yoshida, S. et al. "Nondestructive analyses of unsaturated fatty acid species in dietary oils by attenuated total reflectance with Fourier transform IR spectroscopy," Biopolymers. 2003; 70(4): 604-613. (Year: 2003).*

Sukkasem, C. et al. "Rapid Chemometric Method for the Determination of Oleic and Linoleic Acid in Sunflower Seeds by ATR-FTIR Spectroscopy," Chiang Mai J. Sci. 2015; 42(4): 930-938. (Year: 2015).*

Cozzolino, D. et al. "Evaluation of the use of attenuated total reflectance mid infrared spectroscopy to determine fatty acids in intact seeds of barley (*Hordeum vulgare*)," LWT—Food Science and Technology 56 (2014) 478-483. (Year: 2014).*

Smitt, D.M. et al. "Tissue acquisition and storage associated oxidation considerations for FTIR microspectroscopic imaging of polyunsaturated fatty acids," Vibrational Spectroscopy 60 (2012) 16-22. (Year: 2012).*

Kempfert, K.D. et al. "Detectors for Fourier Transform Spectroscopy," Thermo Nicolet Application Note AN-00125. Thermo Nicolet Spectroscopy Research Center, Madison, WI, USA. Mar. 2002 (Year: 2002).*

Yu, P. et al. "Ultrastructural-chemical makeup of yellow-seeded (*Brassica rapa*) and brown-seeded (*Brassica napus*) canola within cellular dimensions, explored with synchrotron reflection FTIR microspectroscopy," Canadian Journal of Plant Science 2005 v.85 No. 3 pp. 533-541 (Year: 2005).*

Ribeiro, L.F. et al. "Prediction of linolenic and linoleic fatty acids content in flaxseeds and flaxseeds flours through the use of infrared reflectance spectroscopy and multivariate calibration," Food Research International 51 (2013) 848-854 (Year: 2013).*

* cited by examiner

METHODS USING FTIR FOR PLANT TRAIT DETECTION AND TRAIT INTROGRESSION

CROSS-REFERENCE TO RELATED APPLICATIONS

This application claims priority from, and benefit of, U.S. Provisional Application 62/347,728 filed on Jun. 9, 2016. The entire contents of this/these application(s) is hereby incorporated by reference into this application.

BACKGROUND OF THE INVENTION

Certain fatty acids in seeds, including omega-3 fatty acids (for example docosahexaenoic acid or DHA; docosapentaenoic acid or DPA; alpha linolenic acid or ALA; and eicosapentaenoic acid or EPA), continue to gain an increased market appeal due to their health values. Determination of the fatty acid profiles of a population of seeds is laborious and time consuming. The commonly used methods involve sampling seeds and extracting the components of interest from the seed sample for analysis. These methods result in destruction of seeds. Non-destructive analysis of seeds is important because it allows for the selection of events with desired traits while keeping the seeds viable.

U.S. Pat. No. 6,809,819 discloses a method for determining oil content in seeds using evaporative light scattering detection technique. The method involves extracting oil from a seed sample using a solvent, evaporating the solvent in a stream of gas to form oil particles, directing light into the stream of gas and the oil particles to cause a reflected light from the oil particles, and determining the oil content based on the reflected light.

U.S. Patent Publication No. 2012/0092663 discloses a method of analyzing seeds or grains using transmission Raman spectroscopy (TRS) to determine the composition of the seeds such as protein and oil content.

Quantitative analysis of oil or fatty acid content in seeds is often performed using conventional methods, such as near infrared analysis (NIR), nuclear magnetic resonance imaging (NMR), soxhlet extraction, accelerated solvent extraction (ASE), microwave extraction, and super critical fluid extraction. Following the oil extraction, the fatty acid components are hydrolyzed and derivatized prior to be separated by gas or liquid chromatographies. These methods are time consuming and not amenable to high-throughput screening of seeds.

Traits that are continuously varying due to genetic and environmental influences are commonly referred to as "quantitative traits." Quantitative traits may be distinguished from "qualitative" or "discrete" traits on the basis of two factors: environmental influences on gene expression that produce a continuous distribution of phenotypes; and the complex segregation pattern produced by multi-genic inheritance. The identification of one or more regions of the genome linked to the expression of a quantitative trait led to the discovery of Quantitative Trait Loci (QTL). QTLs have been used for trait introgression or other breeding applications on the genetic level. However, decisions for trait introgression or other breeding applications often need to be performed based on compositions of plant seeds instead of genetic analysis.

Therefore, there is the need for inventions that are useful to provide high-throughput, non-destructive, and/or quick turnaround approaches for plant breeding and/or trait introgression.

SUMMARY OF THE INVENTION

Provided are methods and/or systems having advantages of cost effective, time saving, and informative user-friendly characteristics to accomplish trait introgression. The methods provided comprise determining presence of omega-3 fatty acids (for example docosahexaenoic acid or DHA; docosapentaenoic acid or DPA; alpha linolenic acid or ALA; and eicosapentaenoic acid or EPA) using Fourier Transformed Infra Red (FTIR) spectrum. The use of FTIR enables analysis of the oil contained in the seeds using a multivariate-based Mid-FTIR model. The methods and/or systems provided can maintain seed integrity and provide information to facilitate trait introgression and other breeding applications.

This invention is related to methods and systems for determining presence of poly unsaturated fatty acids (PUFAs) in a plant part, accelerating introgression of transgenic plants, and/or eliminating gene silencing of transgenic plants, where Fourier Transform Infra Red (FTIR) spectroscopy is used without evaluating the phenotypes of physical plants. In one aspect, provided is a method for determining presence of poly unsaturated fatty acids (PUFAs) in a plant part. The method comprises:

(a) obtaining a sample of the plant part;
(b) performing a Fourier Transform Infra Red (FTIR) spectroscopy comprising a first absorption band between about 3800 $cm^{-1}$ wavenumber and about 2600 $cm^{-1}$ wavenumber;
(c) comparing the FTIR spectroscopy result of step (b) to existing reference FTIR spectroscopy results; and
(d) predicting whether the sample containing at least one PUFA.

In one embodiment, the method provided further comprises a second absorption band between about 7400 $cm^{-1}$ wavenumber and about 5400 $cm^{-1}$ wavenumber. In another embodiment, the plant part comprises a seed. In a further embodiment, the plant part comprises a canola seed. In another embodiment, the PUFA comprises an omega-3 poly unsaturated fatty acid. In a further embodiment, the omega-3 poly unsaturated fatty acid comprises docosahexaenoic acid (DHA). In another embodiment, the omega-3 poly unsaturated fatty acid is selected from the group consisting of docosahexaenoic acid (DHA), docosapentaenoic acid (DPA), alpha linolenic acid (ALA), eicosapentaenoic acid (EPA), and combinations thereof. In another embodiment, the plant is selected from the group consisting of canola, soybean, sunflower, cotton, Brassica, rapeseed, peanut, corn, wheat, rice, alfalfa, and oat. In another embodiment, the plant is a transgenic plant. In another embodiment, the plant part comprises a transgenic plant cell. In another embodiment, the plant is a back-crossed plant of a first generation, second generation, third generation, fourth generation, fifth generation back-crossing plant, or combinations thereof.

In one embodiment, method is corrected for baseline variations. In another embodiment, method is corrected for water vapor interferences. In a further embodiment, the method is corrected for baseline variations and water vapor interferences. In another further embodiment, the correlation is determined by a model using data that is divided between a calibration set and pre-validation set by a genetic algorithm.

In another aspect, provided is a computerized system for plant trait introgression. The system comprises:
(a) a database comprising existing reference Fourier Transform Infra Red (FTIR) spectroscopy results for samples containing at least one poly unsaturated fatty acid (PUFA) and for samples containing no PUFA;
(b) at least one sample of a plant part;
(c) a customized sample holder made of non-reflective metal alloy; and
(d) an instrument capable of measuring FTIR spectroscopy.

In one embodiment, the FTIR spectroscopy results comprise a first absorption band between about 3800 cm$^{-1}$ wavenumber and about 2600 cm$^{-1}$ wavenumber. In a further embodiment, the FTIR spectroscopy results further comprise a second absorption band between about 7400 cm$^{-1}$ wavenumber and about 5400 cm$^{-1}$ wavenumber. In another embodiment, the plant part comprises a seed. In a further embodiment, the plant part comprises a canola seed. In another embodiment, the PUFA comprises an omega-3 poly unsaturated fatty acid. In a further embodiment, the omega-3 poly unsaturated fatty acid comprises docosahexanoic docosahexaenoic acid (DHA). In another embodiment, the omega-3 poly unsaturated fatty acid is selected from the group consisting of docosahexanoic docosahexaenoic acid (DHA), docosapentaenoic acid (DPA), alpha linolenic acid (ALA), eicosapentaenoic acid (EPA), and combinations thereof. In another embodiment, the plant is selected from the group consisting of canola, soybean, sunflower, cotton, Brassica, rapeseed, peanut, corn, wheat, rice, alfalfa, and oat. In another embodiment, the plant is a transgenic plant. In another embodiment, the plant part comprises a transgenic plant cell. In another embodiment, the plant is a back-crossed plant of a first generation, second generation, third generation, fourth generation, fifth generation backcrossing plant, or combinations thereof.

In another aspect, provided is a method of accelerating introgression of transgenic plants and/or eliminating gene silencing of transgenic plants. The method comprises:
(a) obtaining Fourier Transform Infra Red (FTIR) spectroscopy information from a plant part for a trait of interest;
(b) selecting seeds from the plant providing the plant part and expressing said trait based on the FTIR results from Step (a);
(c) planting the seeds from Step (b);
(d) collecting progeny seeds from Step (c);
and repeating steps (a)-(d) for at least three generations.

In one embodiment, the FTIR spectroscopy results comprise a first absorption band between about 3800 cm$^{-1}$ wavenumber and about 2600 cm$^{-1}$ wavenumber. In a further embodiment, the FTIR spectroscopy results further comprise a second absorption band between about 7400 cm$^{-1}$ wavenumber and about 5400 cm$^{-1}$ wavenumber. In another embodiment, the plant part comprises a seed. In a further embodiment, the plant part comprises a canola seed. In another embodiment, the trait of interest comprises presence of at least one poly unsaturated fatty acid (PUFA). In a further embodiment, the PUFA comprises an omega-3 poly unsaturated fatty acid. In another further embodiment, the omega-3 poly unsaturated fatty acid comprises docosahexaenoic acid (DHA). In another embodiment, the omega-3 poly unsaturated fatty acid is selected from the group consisting of docosahexaenoic acid (DHA), docosapentaenoic acid (DPA), alpha linolenic acid (ALA), eicosapentaenoic acid (EPA), and combinations thereof. In another embodiment, the plant is selected from the group consisting of canola, soybean, sunflower, cotton, Brassica, rapeseed, peanut, corn, wheat, rice, alfalfa, and oat. In another embodiment, the plant is a transgenic plant. In another embodiment, the plant part comprises a transgenic plant cell.

DETAILED DESCRIPTION OF THE INVENTION

Figure 1:
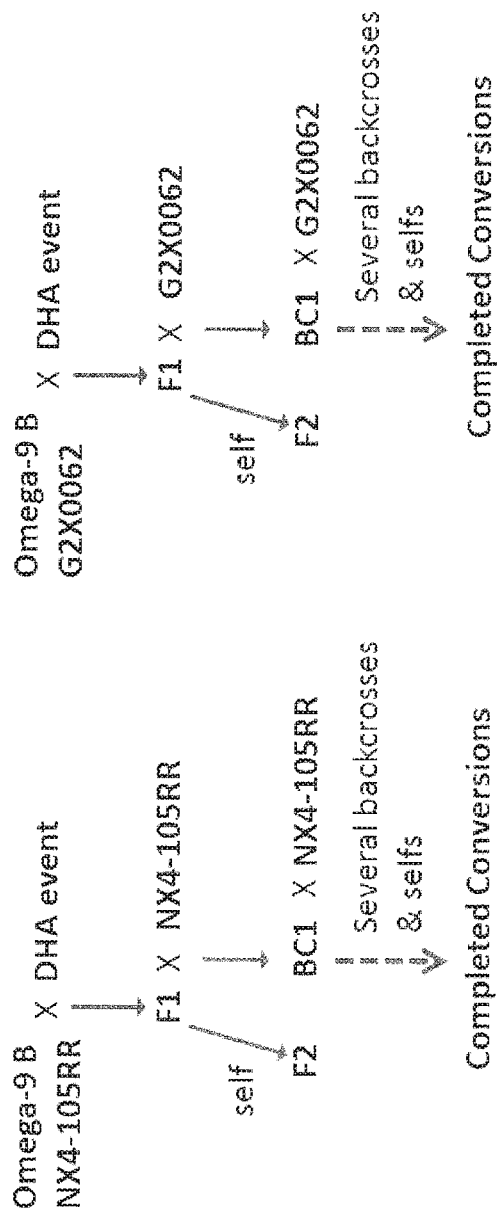
FIG. 1 provides an introgression breeding scheme used in the examples provided. Crossings are performed between DHA transgenic event 035 (homozygous T2 plant) as the male parent and Omega-9 materials as the female parents (NX4-105RR or G2X0062).

Canola seed is a major worldwide source of healthy oil, particularly because it contains a relatively high amount of polyunsaturated fats and relatively low amount of saturated fats. Making healthier oils is a major focus of the food industry. To that end, blending other healthy oils, like low-saturated fat canola oil, with other healthy oils, such as DHA, is becoming more common. Omega-3 fatty acids (for example docosahexaenoic acid or DHA; docosapentaenoic acid or DPA; Alpha linolenic acid or ALA; and eicosapentaenoic acid or EPA) are long chain poly unsaturated fatty acids (PUFAs) necessary for a host of biological functions, and can be implicated in healthy brain development, healthy hearts, and eye development and health. Currently, the best source of omega-3 fatty acids is increasingly available from fish or fish oil.t Some have begun to modify canola such that omega-3 fatty acids (for example DHA) can be produced by the plant itself, removing the necessity for blending, and reducing the cost of omega-3 fatty acids (for example DHA) considerably. However, such efforts to produce omega-3 fatty acids (for example DHA) in plants are frustrated by the long process of breeding, introgressing traits, and selecting for those plants which are most efficient at producing such omega-3 fatty acids (for example DHA). Provided are systems and methods for analyzing whole seeds in a non-destructive manner utilizing Fourier Transformed Infra Red (FTIR) spectrum where the omega-3 fatty acids (for example DHA) content of seeds may be determined prior to planting, thereby reducing the number of steps (and therefore planting seasons necessary) to develop productive canola lines that express high levels of omega-3 fatty acids (for example DHA).

Fourier Transformed Infra Red (FTIR) spectrum is provided as rapid and reliable non-destructive selection method to facilitate accurate and consistent seed selection decisions in introgression populations by quantifying the amount of omega-3 fatty acids (for example DHA) in plant seeds (for example canola seeds). Traditional methods of measuring these properties require larger quantities of harvested grain, planting several thousands of breeding and introgressed populations, sampling the plants 3 weeks after planting, zygosity confirmations in the lab for trait genes, data analysis and reduction, and the elimination of nulls and other populations in order to retain plants only with high omega-3 fatty acids (for example DH A) content. The systems and methods provided herein enable single seed non-destructively using FTIR scanning/screening to eliminate nulls and identify seeds containing desirable content of omega-3 fatty acids (for example DHA) before planting/breeding. Thus the systems and methods provided herein can accelerate plant introgression breeding process, event sorting and event characterization decision process, increase efficiencies and significantly reduce both cost and time.

As used herein, the phrase "about" refers to greater or lesser than the value or range of values stated by 10 percent, but is not intended to designate any value or range of values to only this broader definition. Each value or range of values preceded by the term "about" is also intended to encompass the embodiment of the stated absolute value or range of values As used herein, the phrase "transformed" or "transformation" refers to the introduction of DNA into a cell. The phrases "transformant" or "transgenic" refers to plant cells, plants, and the like that have been transformed or have undergone a transformation procedure. The introduced DNA is usually in the form of a vector containing an inserted piece of DNA.

As used herein, the phrase "transgenic plant" refers to a plant whose genome has been altered by the stable integration of recombinant DNA. A transgenic plant includes a plant regenerated from an originally-transformed plant cell and progeny transgenic plants from later generations or crosses of a transformed plant.

As used herein, the phrase "recombinant DNA" refers to DNA which has been genetically engineered and constructed outside of a cell including DNA containing naturally occurring DNA or cDNA or synthetic DNA.

As used herein, the phrase "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, the phrase "phenotype" refers to the detectable characteristics of a cell or organism which are a manifestation of gene expression.

As used herein, the phrase "elite line" refers to any line that has resulted from breeding and selection for superior agronomic performance. An elite plant is any plant from an elite line.

As used herein, the phrase "plant" includes dicotyledons plants and monocotyledons plants. Examples of dicotyledons plants include tobacco, *Arabidopsis*, soybean, tomato, *papaya*, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale.

As used herein, the term "plant" also includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

As used herein, the phrase "trait" refers to a physiological, morphological, biochemical, or physical characteristic of a plant or particular plant material or cell. In some instances, this characteristic is visible to the human eye, including seed or plant size, or can be measured by biochemical techniques, including detecting the protein, starch, or oil content of seed or leaves, or by observation of a metabolic or physiological process (e.g., by measuring uptake of carbon dioxide), or by the observation of the expression level of a gene or genes (e.g., by employing Northern analysis, RT-PCR, microarray gene expression assays), or reporter gene expression systems, or by agricultural observations including stress tolerance, yield, or pathogen tolerance.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

FTIR mode of operations—Canola (*Brassica napus*) seeds are placed in a custom designed 96 microtiter plates. The plate material is made of non-reflective metal alloy with indentations to contain the round seed. The loaded plates are then introduced into a Bruker Fourier Transform Infra Red (FTIR) instrument comprising a Vertex Tensor 27 equipped with a HTS-XT plate reader. The MCT (model 316) detector is cooled using liquid nitrogen and the intensity of a total reflective surface (gold target) is used to calibrate the system.

The FTIR scans are conducted in the wavenumber range between 7500 $cm^{-1}$ and 600 $cm^{-1}$ with a resolution of 8 $cm^{-1}$ and a mirror velocity of 20 KHz. Thirty two successive scans are acquired and the average per sample is used for the chemometric prediction. The system is controlled by OPUS 7.0 software. The calibration model is built in OPUS using Quant 2 workflow. A first derivative with 17 smoothing points and multiplicative scattering correction (MSC) are applied to generate the calibration spectra. This calibration is validated to provide an $R^2$ value of 90.56, a RMSEP of 0.438, and a RPD of 3.27.

Models—Canola (*Brassica napus*) single seeds from different varieties are weighted and then scanned using FTIR followed by determination of their oil content and fatty acid relative amounts using a separate method (for example as disclosed in U.S. Patent Publication No. US 2014/0359900 A1). The DHA content (weight % of lipid) is then reported and introduce in OPUS Quant2 (Bruker Optics Ltd).

TABLE 1

Representative relative composition of fatty acids (mean % shown)

| Sample Name | C22:6 (%) | C18:1 (%) | C18:3 (%) | TSFA (%) | Oil (%) |
|---|---|---|---|---|---|
| DH12075 segregant | 0.0 | 72.0 | 2.1 | 7.1 | 40.9 |
| Historical line Field grown | 0.0 | 71.8 | 1.8 | 6.8 | 42.0 |
| Historical line GH grown | 0.0 | 73.3 | 2.0 | 7.0 | 33.2 |
| PUFA synthase transgenic | 1.5 | 65.1 | 5.8 | 7.5 | 35.6 |
| Low TSFA transgenic | 0.0 | 76.8 | 2.8 | 4.0 | 38.8 |

Table 1 shows a representative relative composition for selected fatty acids (C22:6, C18:1 and C18:3, Total Saturated Fatty Acids) and oil content based on quantitated Fatty Acid Methyl Esters (FAMEs) relative to seed weight. Total Saturated Fatty Acid (TSFA) is the sum of C14:0, C16:0, C18:0, C20:0, C22:0 and C24:0. The majority of the seeds introduced in the model are transgenic seeds resulting from the expression of PUFA synthases (2696 seeds). The low TSFA seeds are grown in green houses from transgenic events expressing a fungal fatty acid desaturase. Those seeds add more variability in the TSFA content but also increase the C18:1 content. Dow AgroSciences canola proprietary lines are selected to add variability in the C18:1 and C18:3 relative content. Finally Field and green house grown seeds are also added to the model to add variability in oil content (25% to 42%). All these variations in oil quantity and quality enable the model to be more robust for further introgression of DHA trait in conventional or high oleic canola lines.

Figure 2:
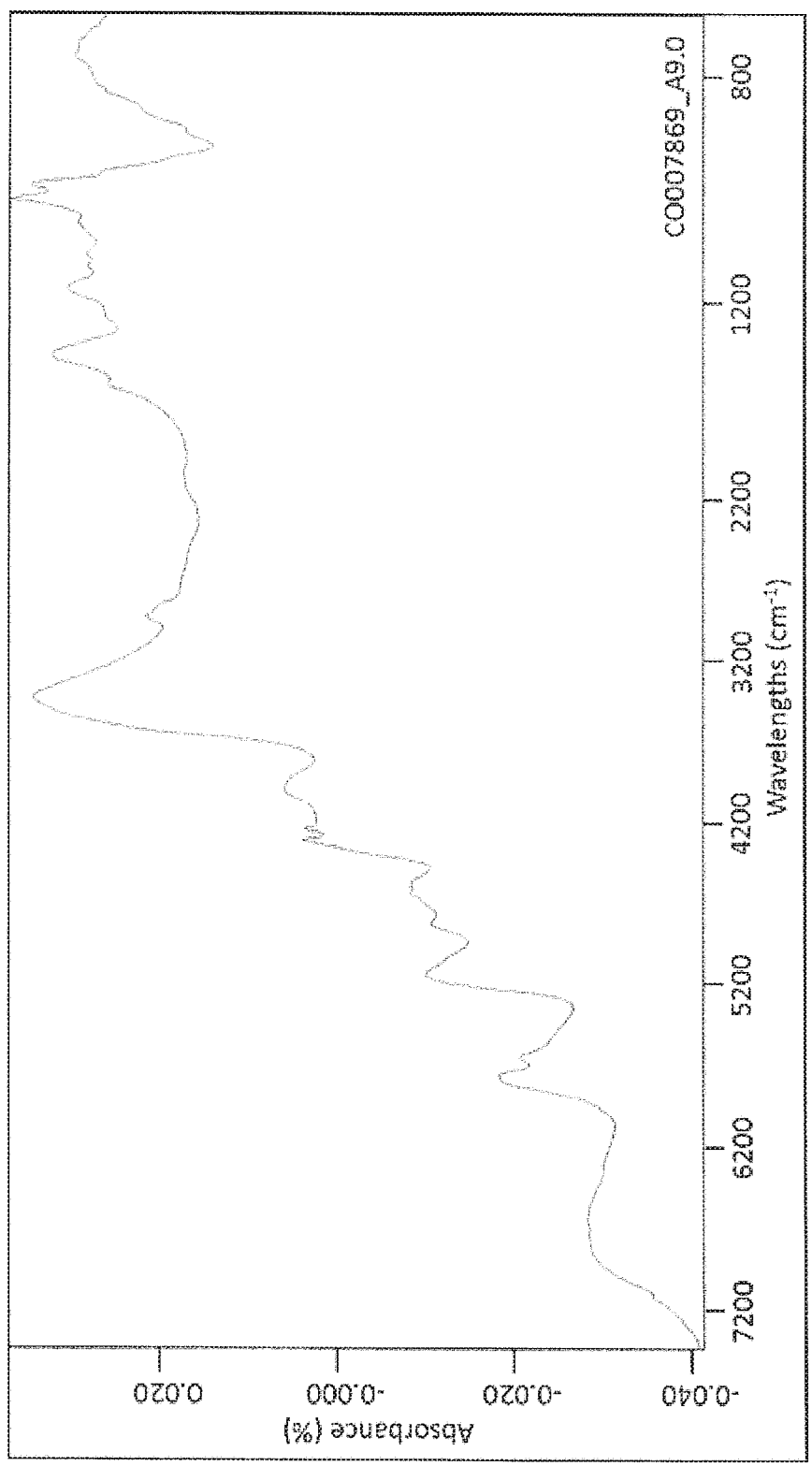
FIG. 2 shows a representative FTIR spectrum for a canola seed containing a desirable DHA content (in this case about 5% by weight of the lipid within the seed).
Figure 3:
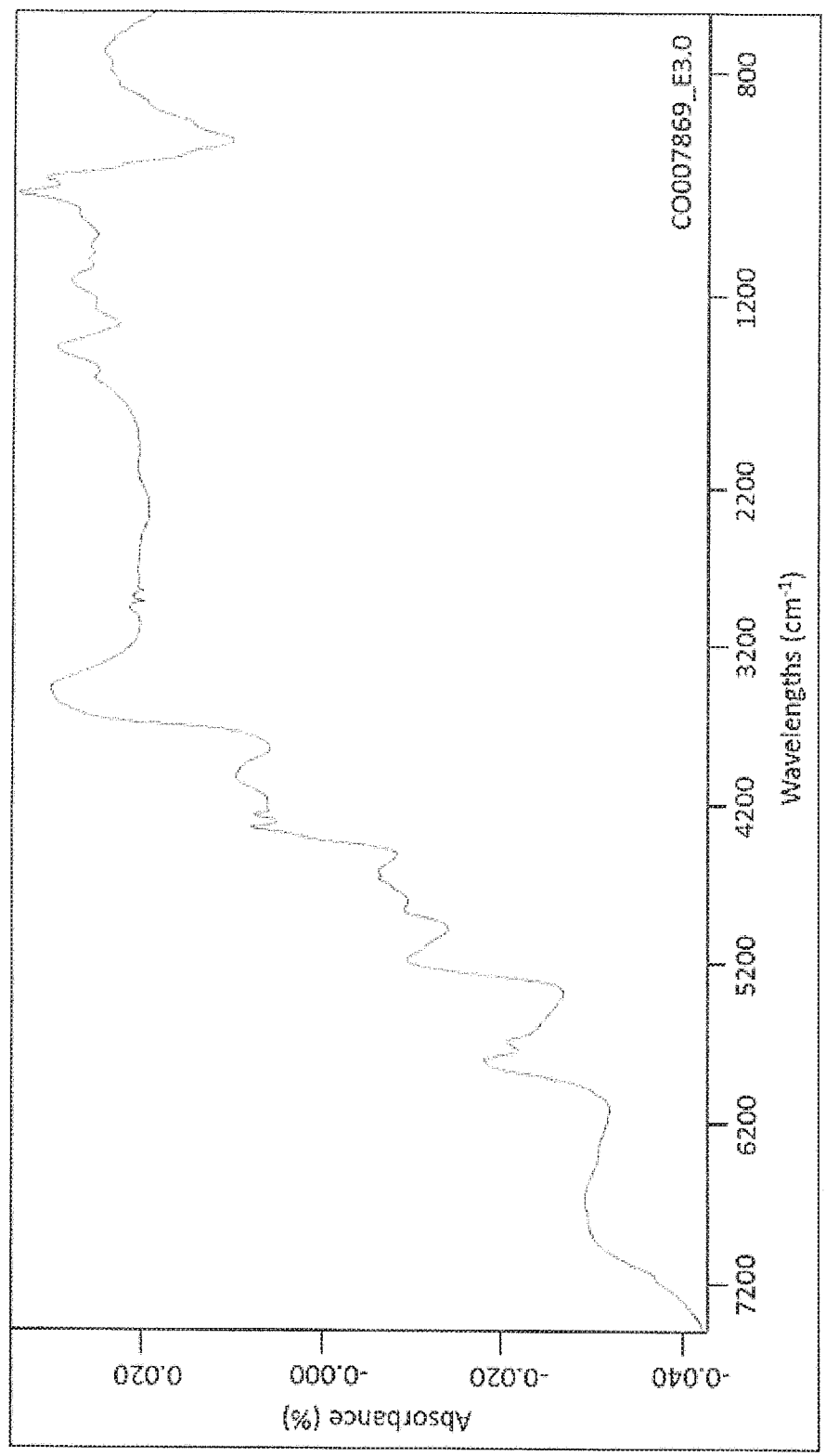
FIG. 3 shows a representative FTIR spectrum for a canola seed containing no detectable DHA (i.e., about 0% by weight of the lipid within the seed).

FIG. 2 shows a representative FTIR spectrum for a canola seed containing a desirable DHA content (in this case about 5% by weight of the lipid within the seed). FIG. 3 shows a representative FTIR spectrum for a canola seed containing no detectable DHA (i.e., about 0% by weight of the lipid within the seed).

Example 2

Crossings are performed between DHA transgenic event 035 (homozygous T2 plant) as the male parent and Omega-9 materials as the female parents (NX4-105RR or G2X0062) as illustrated in FIG. 1. Crossings are performed between DHA transgenic event 035 (homozygous T2 plant) as the male parent and Dow AgroSciences Omega-9 materials as the female parents (DAS Omega-9 commercial variety NX4-105RR or DAS Omega-9 canola inbred G2X0062). G2X0062 inbred has been described in U.S. Pat. Nos. 8,558,065 and 8,530,726. DHA transgenic event 035 has been described in international patent application publication WO 2015/081270.

Fourier Transform Infra Red (FTIR) scanned is performed as set forth in Example 1 and such FTIR results show that the DHA trait in the F1 behaves as semi-dominant as compared to both the parents and all F1's are hemizygous for the DHA trait as expected. Accordingly, FTIR results are used to predict trait genetics and DHA seed selections of F1 harvested seeds before planting. DHA outliers which do not contain DHA (since crossing is a manual pollination process) are eliminated before planting.

Further, BC1F1 seeds are obtained by crossing hemizygous F1 plant with Omega-9 parents as shown in FIG. 1. As expected from Mendelian inheritance of single locus, 50% of the BC1F1 seeds contain at least 1 copy of the DHA transgene (DHA presence) and 50% of the BC1F1 seeds contain no detectable DHA. From these FTIR scans, DHA predictions are determined where BC1F1 seeds containing DHA and BC1F1 seeds containing no DHA are planted separately for DHA transgene molecular confirmation. Molecular confirmation of DHA genes are performed based on 5 DHA transgene assays, Pfa1, Pfa2, Pfa3, HetI and Pat, as previously disclosed in International Patent Publication No. WO 2015/081270 A1. Table 2 shows the results of the BC1F1 seeds, where plants from BC1F1 seeds containing DHA as determined by FTIR are 100% positive after molecular confirmation of DHA genes, validating the FTIR screening results. Similarly, plants from BC1F1 seeds containing no DHA as determined by FTIR are 100% negative after molecular confirmation of DHA genes, again validating the FTIR screening data (data not shown). Accordingly, BC1F1 seeds with the highest DHA % based on the FTIR results are selected for advancement to the next introgression generations to produce the F2 generation.

TABLE 2

Summary of FT1R scanning results on BC1F1 seeds and molecular confirmation of DHA genes

| BC1F1 seeds | Total seeds scanned by FTIR | Seeds containing DHA determined by FTIR | Seeds planted and sampled | Plants with molecular confirmation of DHA genes |
|---|---|---|---|---|
| 035 x NX4-105RR | 530 | 212 | 211 | 211 |
| 035 x G2X0062 | 530 | 136 | 123 | 123 |

Next, FTIR analysis is performed on the F2 population for the prediction of DHA. A total of 1174 F2 seeds are scanned and planted for NX4-105RR background and a total of 902 F2 seeds are scanned and planted for G2X0062 background (resulting a total of 2076 F2 seeds for FTIR scan and molecular confirmation of DHA genes). The results confirm that FTIR scanning facilitates the selection of the highest DHA containing seed to enrich the population in homozygous state and to eliminate ~50% of the F2 population before planting. The FTIR-based F2 selections enable reduction of the number of seeds to be planted by at least 75% which accelerated the entire introgression/breeding process and reduce required greenhouse space at the same time. In addition, further data show that the selection of DHA-positive transgenic plants can be enriched by selecting above 0.75% DHA (elimination of nulls) based on FTIR scanning.

We claim:

1. A method for determining presence of docosahexaenoic acid (DHA) in a viable whole plant seed, the method comprising
   (a) obtaining one or more viable whole plant seeds;
   (b) performing a Fourier Transform Infrared (FTIR) spectroscopy analysis of each of the one or more viable whole plant seeds, wherein the spectroscopy analysis comprises use of a detector cooled using liquid nitrogen to detect absorbance at a first absorption band between about 3800 $cm^{-1}$ wavenumber and about 2600 $cm^{-1}$ wavenumber;

(c) comparing the absorbance of step (b) to existing reference FTIR absorbance;
(d) selecting at least one of the one or more viable whole plant seeds analyzed in step (b) based on the detected absorbance of step (b), wherein each selected seed is viable and predicted to contain DHA based on the detected absorbance of step (b); and
(e) planting or breeding with the at least one seed selected in step (d).

2. The method of claim 1, further comprising using the detector to detect absorbance at a second absorption band between about 7400 $cm^{-1}$ wavenumber and about 5400 $cm^{-1}$ wavenumber.

3. The method of claim 1, wherein the one or more viable whole plant seeds obtained in (a) are from a plant selected from the group consisting of canola, soybean, sunflower, cotton, *Brassica*, rapeseed, peanut, corn, wheat, rice, alfalfa, and oat.

4. The method of claim 1, wherein the one or more viable whole plant seeds obtained in (a) are *Brassica napus* seeds.

5. The method of claim 1, wherein the one or more viable whole plant seeds obtained in (a) are from a transgenic plant.

* * * * *